United States Patent [19]

Forni

[11] 4,449,933
[45] May 22, 1984

[54] INTERPROXIMAL DENTAL STIMULATOR AND CLEANING APPARATUS

[76] Inventor: William J. Forni, 2911 Montecito Ave., Santa Rosa, Calif. 95404

[21] Appl. No.: 344,312

[22] Filed: Feb. 1, 1982

[51] Int. Cl.³ .............................................. A61L 3/00
[52] U.S. Cl. ..................................... 433/141; 433/149
[58] Field of Search ............... 433/142, 141, 148, 147; 128/62 A; 132/93, 89; 15/167 R, 167 A

[56] References Cited

U.S. PATENT DOCUMENTS

| | | | |
|---|---|---|---|
| 2,016,597 | 10/1935 | Drake | 433/142 |
| 3,815,243 | 11/1974 | Eames | 433/149 |
| 3,890,714 | 6/1975 | Gores | 433/149 |
| 3,939,520 | 2/1976 | Axelsson | 132/93 |
| 4,222,143 | 9/1980 | Tarrson | 132/89 |

Primary Examiner—Robert Peshock
Attorney, Agent, or Firm—Limbach, Limbach & Sutton

[57] ABSTRACT

An interproximal dental stimulator and cleaning apparatus having a handle and a flexible member, the flexible member including two wing-like structures which project outwardly from the longitudinal axis of the flexible member, the amount of projection tapering from the base of the member to the tip of the member, so that the member has the general shape of an arrowhead and so that when the member is inserted between adjacent teeth, the wing-like structures conform to the shape of the interproximal gingival papilla, and the structures are thus permitted to occupy the dental sulcus between the papilla and associated teeth.

33 Claims, 14 Drawing Figures

U.S. Patent  May 22, 1984  Sheet 1 of 3  4,449,933
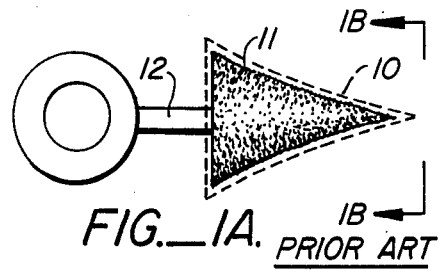
FIG._1A. PRIOR ART
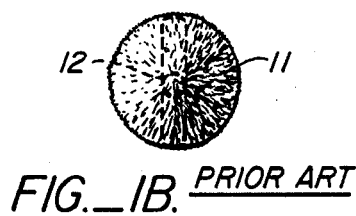
FIG._1B. PRIOR ART
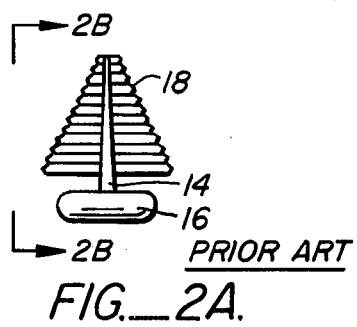
FIG._2A. PRIOR ART
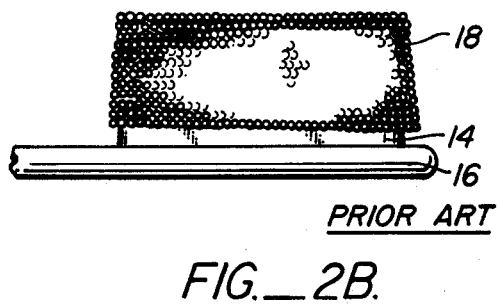
FIG._2B. PRIOR ART
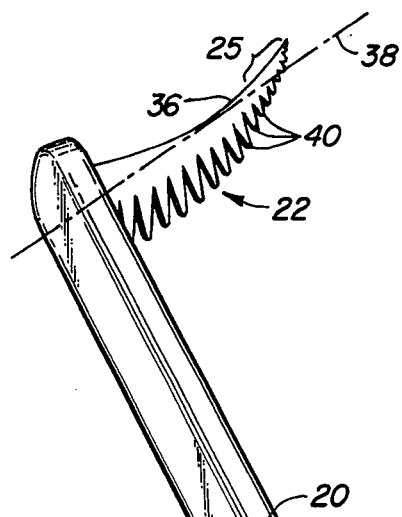
FIG._3.
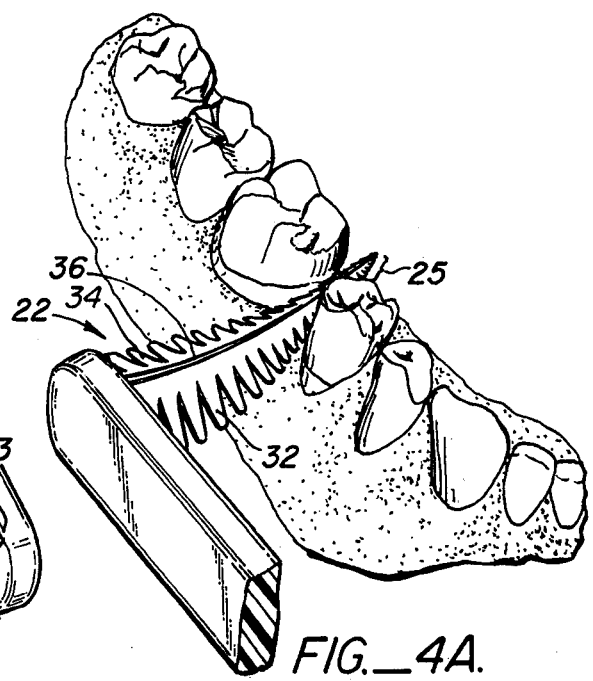
FIG._4A.

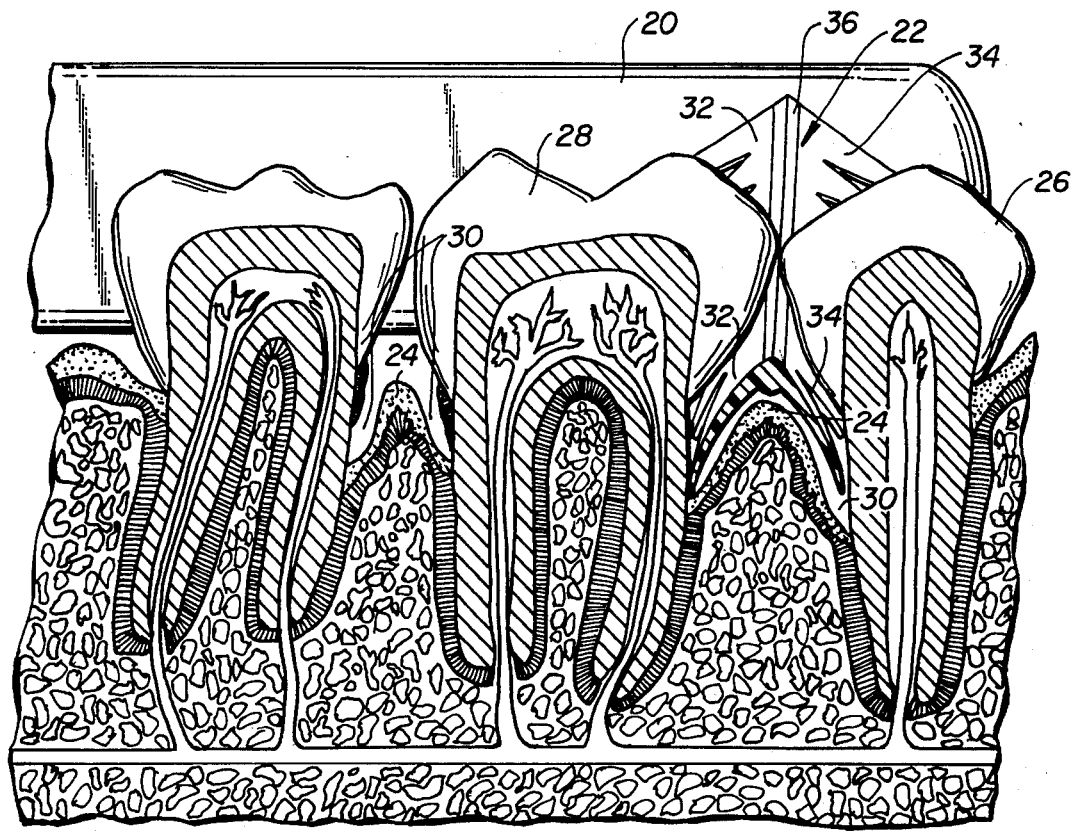
FIG._4B.
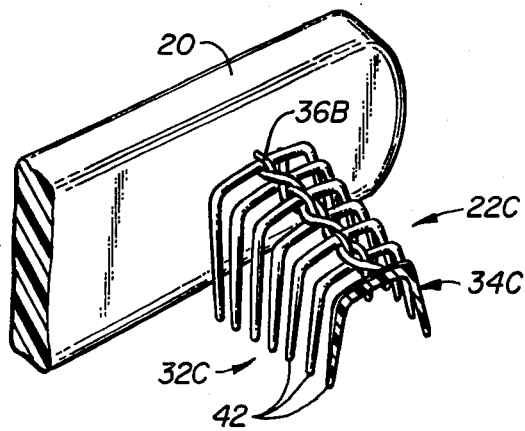
FIG._6C.
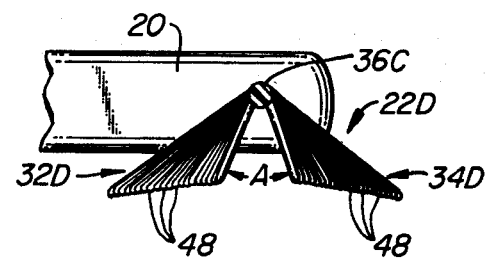
FIG._6D.
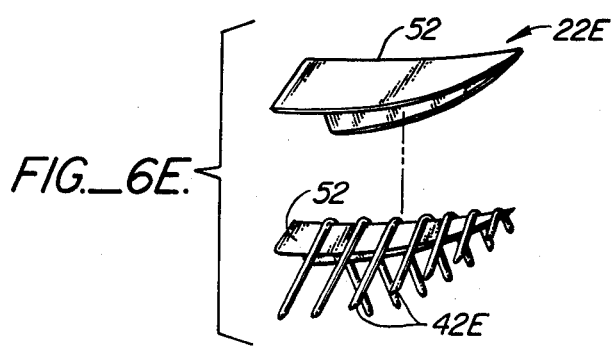
FIG._6E.

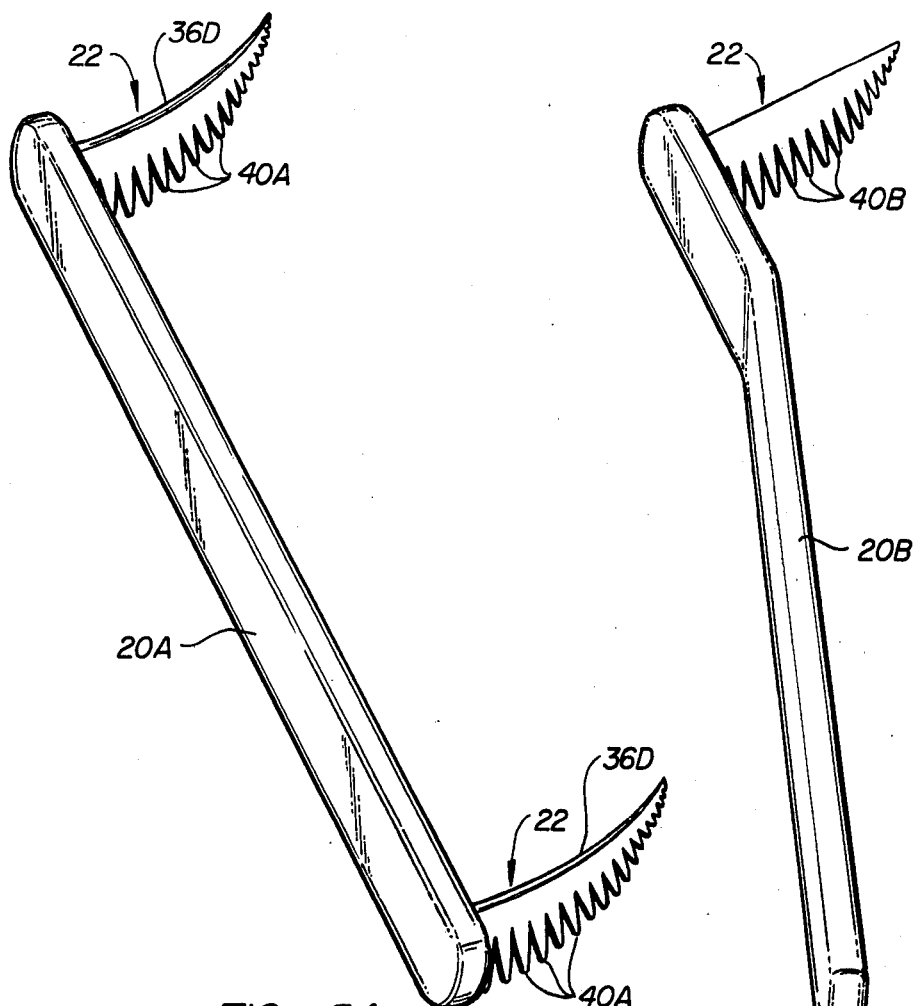
FIG._5A.
FIG._5B.
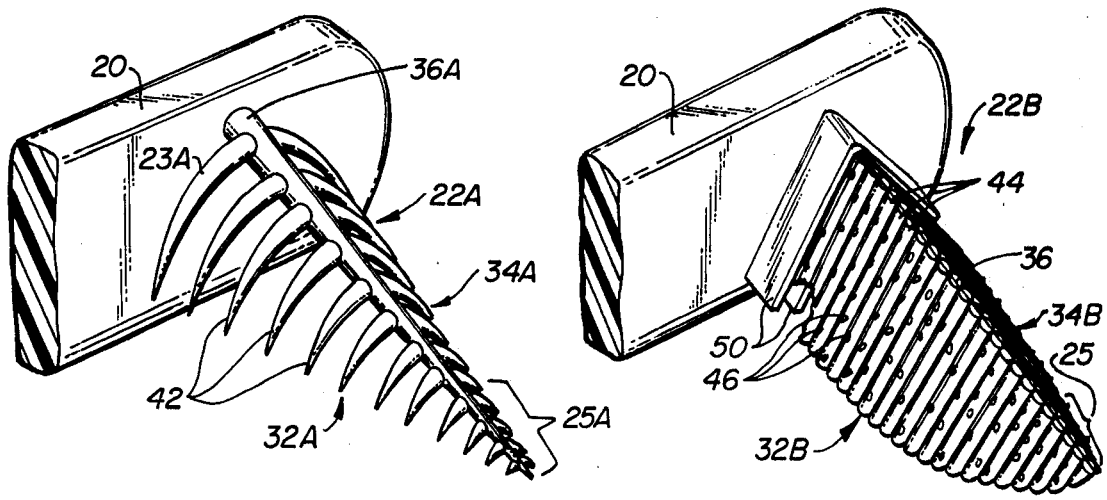
FIG._6A.
FIG._6B.

INTERPROXIMAL DENTAL STIMULATOR AND CLEANING APPARATUS

BACKGROUND OF THE INVENTION

The invention relates generally to an apparatus for the care and maintenance of human teeth and gums and, particularly, to apparatus for cleaning and stimulating the region between a tooth and adjacent interproximal gingival papilla.

The general structure of teeth and gum in the human mouth takes the form of abutting tooth structures, partially embedded in bone, with the interproximal region between adjacent teeth being generally filled with gingival papilla or gum structure. Where there has been periodontal surgery or periodontal disease, the gingival papilla and bone structure, which formerly filled the interproximal region, will have deteriorated significantly. The result is an interproximal space which provides an excellent environment for accumulation of food particles and the build up of bacteria or plaque. A vertical cross-sectional view of this interproximal space resembles a triangle in the region above the undiseased gum line. Below the gum line, the interproximal space resembles furrows extending along each tooth root and separated by a mound of gingival papilla. These furrows of space will be hereinafter referred to as the dental "sulcus" between a tooth and adjacent gingival papilla.

It is common knowledge that the build-up of plaque on the surface of a tooth is significant contributor to tooth decay, as well as associated tooth and gum diseases. The brushing of one's teeth with the standard toothbrush design is often recognized as being inadequate to remove plaque from all surfaces of a tooth especially those surfaces facing an adjacent tooth, as well as those surfaces in the dental sulcus between the tooth and the interproximal gingival papilla.

Flossing is recognized as one method for gaining access to the dental sulcus. However, flossing is often inconvenient and difficult.

In the past, toothbrush designs have been suggested for gaining access to and for cleaning these interproximal areas. Among the suggested designs are those disclosed in U.S. Pat. No. 3,939,520 to Axelsson and U.S. Pat. No. 3,720,975 to Nelson. In the Axelsson patent is disclosed a toothbrush with parallel bristles which extend in opposite directions from a central fin. Positioned at right angles to the fin is a flat base. The toothbrush is shaped so that, in use, the base of the fin is positioned on top of the gingival papilla and the bristles occupy the space above the base in the triangular portion of the interproximal space.

In the Nelson patent, a toothbrush is disclosed which has a conical shape provided by bristles which extend radially from a central core and which taper in length to form a tip. In the Nelson patent, the shape of the brush permits easy insertion of the brush between adjacent teeth. However, as in the Axelsson patent, the toothbrush in the Nelson patent causes the gingival papilla to be compressed.

As a result of the compression of the gingival papilla the dental sulcus between the tooth and adjacent gingival papilla becomes obstructed and is sealed from access by the cleaning structures or bristles of the brush designs. Thus, the above designs are not entirely satisfactory for the complete cleaning and/or stimulation of the tooth and associated structures.

This is especially true where periodontal surgery has been performed or where there is moderate to severe periodontal recession. In these cases, a distinct space or sulcus forms between the tooth and adjacent gingival papilla. In order to maintain and increase the degree of oral hygiene and to prevent progression of periodontal disease, an interproximal brush is needed which is shaped to fit over the interproximal gingival papilla and into the sulci approximating the teeth, without compressing the interproximal gingival papilla.

The present invention provides such a brush design.

SUMMARY OF THE INVENTION

The foregoing and other problems of prior art toothbrushes are overcome by the present invention of an interproximal dental stimulator and cleaning apparatus of the type which is manipulated by handle means, and which is used in the dental sulcus region between a tooth and adjacent interproximal gingival papilla. The apparatus includes a flexible member which has a generally arrowhead-like shape. The member has first and second elongated, wing-like structures which extend from the broad end of the flexible member to the tip of the flexible member and along the longitudinal axis of the flexible member. These wing-like structures project outwardly from the longitudinal axis for a distance which is larger at the broad end of the member and which decreases in magnitude toward the tip. Each wing-like structure provides cleaning and stimulating surfaces. In one embodiment, the wing-like structures are disposed with respect to one another so that a cross-section of the member taken at right angles to the longitudinal axis of the flexible member resembles a "V". Because of the flexible nature of the member and the winged structure provided, the interproximal gingival papilla is accepted between the winged structures, rather than compressed by the winged structures upon insertion of the member between adjacent teeth. As such, the wing-like structures occupy and can be manipulated within the dental sulcus regions between the papilla and the teeth.

It is, therefore, an object of the present invention to provide an interproximal dental stimulator and cleaning apparatus which is capable of cleaning and stimulating the dental sulcus region between a tooth and adjacent interproximal gingival papilla.

It is a further object of the present invention to provide an interproximal dental stimulator and cleaning apparatus which, when being used to clean and stimulate the dental sulcus region between a tooth and adjacent interproximal gingival papilla, conforms to the shape of the interproximal gingival papilla.

It is another object of the present invention to provide an interproximal dental stimulator and cleaning apparatus which includes a flexible member, having a generally arrowhead-like shape, the flexible member having first and second elongated wing-like structures which extend along the longitudinal axis of the flexible member, and which project outwardly from the longitudinal axis, tapering in outward projection from the broad end of the member to the tip, and wherein each wing-like structure provides cleaning and stimulating surfaces, so that the apparatus can be inserted between adjacent teeth such that the intergingival papilla is accepted between the wing-like structures and the wing-like structures themselves occupy and can be manipulated within the dental sulcus region between the papilla and teeth.

It is a still further object of the present invention to provide an interproximal dental stimulator and cleaning apparatus having a generally arrowhead-like shape and wing-like structures which, when inserted between adjacent teeth, will conform to the shape of the interproximal gingival papilla.

It is a still further object of the present invention to provide an interproximal dental stimulator and cleaning apparatus which permits the cleaning and stimulating of the dental sulcus region resulting from periodontal surgery or moderate to severe periodontal disease.

It is another object of the present invention to provide an interproximal dental stimulator and cleaning apparatus which is anatomically shaped to fit the shape of the interproximal gingival papilla.

The foregoing and other objectives, features and advantages of the invention will be more readily understood upon consideration of the following detailed description of certain preferred embodiments of the invention, taken in conjunction with the accompanying drawings.

BRIEF DESCRIPTION OF THE DRAWING

FIG. 1A is a side elevational view of a prior art toothbrush.

FIG. 1B is an end elevational view of the prior art toothbrush illustrated in FIG. 1A, taken along line 1B–1B in the direction of the arrows.

FIG. 1A is an end elevational view of another prior art toothbrush.

FIG. 2B is a side elevational view of the prior art toothbrush illustrated in FIG. 2A, taken along line 2B–2B in the direction of the arrows.

FIG. 3 is a perspective view of the present invention.

FIG. 4A is a perspective view of the flexible member of the present invention after insertion into the region between the adjacent teeth.

FIG. 4B is an enlarged elevational sectional view of the present invention illustrating the conformance of the flexible member of the present invention to the shape of the interproximal gingival papilla.

FIG. 5A illustrates an alternative embodiment of the present invention where two flexible members are positioned on a handle to provide a correctly orientated flexible member for the various tooth positions in the human jaw.

FIG. 5B illustrates an alternative embodiment of the present invention illustrating an angled handle which assists in the proper positioning of the flexible member with respect to the tooth and papilla being cleaned and stimulated.

FIG. 6A illustrates an alternative embodiment of the flexible member, wherein each wing-like structure comprises a row of bristles, the lengths of which taper to form a tip.

FIG. 6B is an illustration of an alternative embodiment of the present invention, wherein the wing-like structures comprise sheets of flexible material having a pattern of raised surfaces thereon.

FIG. 6C is an elevational sectional view of an alternative embodiment of the present invention, wherein the wing-like structures include a rib of twisted wire and are shaped to provide a "U" shaped cross section at right angles to the rib.

FIG. 6D is an elevational sectional view showing a "V" shaped cross section which decreases in angle toward the tip of the flexible member.

FIG. 6E is an exploded view of an alternative embodiment.

DETAILED DESCRIPTION OF THE PREFERRED EMBODIMENTS

FIGS. 1A and 1B provide end and side elevational views of a toothbrush design disclosed in the Nelson patent, as discussed above. As can be appreciated from these figures, the toothbrush of the Nelson patent is essentially conical in shape (see dotted lines 10) with bristles 11 extending outwardly from a central stem 12. Because of this conical shape, the brush, when inserted between adjacent teeth, will cause the interproximal gingival papilla to be compressed, thus sealing the dental sulcus regions from access by the bristles of the brush.

FIGS. 2A and 2B provide end and side elevational views of the toothbrush disclosed by the Axelsson patent. An attachment plate 14 is attached at right angles to a base plate 16. Bristles 18 project at right angles to the attachment plate 14, both along the height of length of the attachment plate 14. As a result, a wedge-shaped brush is obtained as illustrated in the figures. In use, the base plate 16 rests upon the interproximal gingival papilla with the bristles 18 occupying the space between the adjacent teeth. The papilla is thus compressed and the dental sulcus between the tooth and adjacent papilla sealed from access by the bristles 18 of the brush.

In FIG. 3, the present invention is illustrated which avoids the compression effect of the brushes of the Nelson and the Axelsson patents. A handle 20 is provided to which is attached flexible member 22. The flexible member 22 has an arrowheadlike shape in plan view. The broad end or base 23 of the flexible member 22 is attached to an end of the handle 20 with free end or tip portion 25 spaced outwardly from the handle 20. The tip portion 25 of the member 22 aids in the insertion of the member between adjacent teeth as illustrated in FIG. 4A.

FIG. 4B illustrates the conformance of the flexible member 22 to the shape of the gingival papilla 24 which is located between adjacent teeth 26 and 28, for example. From FIG. 4B, it can be seen that because the flexible member 22 conforms to the shape of the gingival papilla, the gingival papilla is not compressed and the structures of the member 22 can occupy the dental sulcus 30.

Referring to FIGS. 3, 4A and 4B, the construction of the flexible member 22 will be described in greater detail. One of the principal requirements of the flexible member is that a structure be provided which has a shape similar to the interproximal gingival papilla, or which is conformable, upon insertion between adjacent teeth, to the shape of the gingival papilla. FIG. 3 illustrates one embodiment by which the above requirements can be met. The flexible member 22 is made up of two wing-like structures 32 and 34. Each wing-like structure is elongated, has a broad end and tapers to a tip. The structures 32 and 34 share a common longitudinal junction 36 which lies approximately along the longitudinal axis 38 of the flexible member 22.

In the embodiment illustrated in FIG. 3, the junction of wing-like structures 32 and 34 is shown to be curved, rather than a straight line. In FIG. 3, the junction 36 curves in a direction away from the direction in which the wing-like structures 32 and 34 project. This curvature is especially useful in transforming the rotational motion of the human wrist into a lineal movement of the flexible member within the dental sulcus 30.

While FIG. 3 illustrates a curved junction 36, it is not necessary for satisfactory operation of the present invention that the junction be curved. Alternative embodiments will be discussed in the following paragraphs.

The wing-like structures 32 and 34 shown in FIGS. 3, 4A and 4B can be constructed of any flexible, resilient material, such as plastic or nylon. The material can be molded or cut, or shaped through appropriate means, to provide cleaning and stimulating surfaces 40, FIG. 3. In this embodiment, the cleaning and stimulating surfaces are provided by fingers 40 or teeth cut into the wing-like structures. The fingers are longest toward the base 23 of the member 22 and taper in length toward the tip portion 25 of the member 22. As can be seen from FIG. 3, the fingers 40 have tips which are "squared-off". Other suitable shapes include rounded tips 40A, FIG. 5A, or slightly pointed tips 40B, FIG. 5B.

It will be noted that in FIG. 3, wing-like structure 32 is positioned with respect to wing-like structure 34 so that a cross-section taken at right angles to the longitudinal axis 38 of the member 22 resembles a "V" shape. This "V" shape is also illustrated in FIG. 4B.

A further satisfactory cross-sectional design is a "U" shape, FIG. 6C.

FIGS. 6A and 6B illustrate alternative embodiments for the wing-like structures 32A and 34A. In FIG. 6A, a row of bristles 42 form each wing-like structure. As before, the bristles 42 are longest at the base 23A of the member 22A and shortest at the tip portion 25A. The common junction 36 at which the bristles are affixed can be a twisted wire 36B, FIG. 6C, a rib 36A, FIG. 6A, or other suitable supporting structure. The bristles 42 can be of uniform cross section, or, as shown in FIG. 6A, have a thicker cross section adjacent the rib 36A than at the free end of the bristle.

FIG. 6B illustrates an embodiment in which the wing-like structures 32B and 34B are constructed of sheets of flexible material which have a pattern of raised surfaces 44 and/or irregularities 46 so as to present a cleaning and stimulating surface. Irregularities 46 can take the form of a bumpy surface or abrasive particles. One such pattern includes a series of ridges 44 extending at right angles from the junction 36. As before, the wing-like structures are widest at the base 23B of the member and taper to a minimum toward the tip portion 25B.

In both FIGS. 6A and 6B, the "V" cross-sectional wing orientations are shown.

FIGS. 3, 5A and 5B illustrate various configurations of handles 20, 20A, and 20B and flexible member 22. In FIG. 3, a first flexible member 22 is positioned at one end of the handle 20 with winglike structures 32 and 34 projecting downward. A second flexible member 22 is positioned at the opposite end and opposite side of the handle 20 with wing-like structures 32 and 34 projecting upward. This configuration provides a properly oriented flexible member 22 for all teeth locations in the human jaw. For example, the flexible member 22 at the top of the handle of FIG. 3 can be used with teeth positioned at the lower righthand portion and, by a 180 degree rotation about the longitudinal axis of the handle 20, the upper lefthand portion of the jaw. The flexible member 22 at the bottom of the FIG. can be used in lower lefthand portion and, by a 180 degree rotation about the longitudinal axis of the handle 20, the upper righthand jaw position.

In FIG. 5A, a flexible member 22 is positioned at each end of the handle 20A on the same side of the handle and so that the wing-like structures of both members project in the same direction.

In this configuration, all teeth positions on a jaw can be accessed without rotating the handle 20. In use, the handle 20A is grasped between thumb, index finger and middle finger. If the member 22 at the top of the figure were being used to clean positions in the lower righthand jaw, for example, only a slight rotation of the wrist is necessary to move the other flexible member into position for use on teeth positions in the lower lefthand jaw. With the configuration of FIG. 3, a 180 degree rotation about the longitudinal axis is needed, in addition to the slight rotation of the wrist, in order to access teeth positions on opposite sides of opposite jaws.

FIG. 5B shows the handle 22B to be angled at a predetermined distance from a point at which the flexible member 22 is attached to the handle 20B. The angling of the handle further assists in the proper orientation of the flexible member 22 with respect to the teeth and papilla being cleaned or stimulated.

In operation as best shown in FIGS. 4A and 4B, the tip of the flexible member is initially inserted into the space between adjacent teeth. As the flexible member is further inserted into the space the longitudinal junction 36 is guided over the papilla and the wing-like structures 32 and 34 are guided between the papilla 24 and the adjacent teeth 26 and 28. As this occurs, the papilla 24 is encased between the wing-like structures 32 and 34 and the wing-like structures enter the dental sulcus region 30 between the papilla 24 and the adjacent teeth. Because the outward projections of the wing-like structures taper from a minimum at the tip 25 to a maximum at the base 23 of the flexible member 22, the movement of the wing-like structures into the dental sulcus is gradual and, thus, less painful. Additionally, the distance into the dental sulcus region 30 which the flexible member 22 is inserted determines the depth through which the wing-like structures will extend within the dental sulcus region 30. Because the depth of dental sulcus 30 differs from tooth to tooth, this tapered feature permits the invention to be useful in most applications. Where the depths of the sulcus on either side of the papilla differ, the wing-like structures of the flexible member can be trimmed as required.

As will be recognized to one skilled in the art, the flexible member 22 can be easily constructed using any one of a number of techniques. One such technique, illustrated in FIG. 3, is to form each wing-like structure separately and to bond the structures together, along a reinforcing rib or central body, see 36A in FIG. 6A, 36C in FIG. 6D and 36D in FIG. 3. Alternatively, one could use a one-piece sheet of flexible material, form the fingers appropriately, and then fold the sheet along the longitudinal axis according to the desired angle, as in FIGS. 5B and 6B, for example. The handle and flexible members could also be molded as one piece. In such configuration, a reinforcing structure could be placed in the handle portion to stiffen the handle 20.

In addition to bonding the flexible member 22 to the handle 20, the base 23 of the flexible member 22 can be sandwiched between a pair of angled brackets 50 which are attached to the handle 20. (FIG. 6B.) In this manner the anatomical orientation of the wing-like structures 32 and 34 can be automatically fixed as part of the assembly process.

From another perspective, the present invention in the embodiment of FIG. 6A, for example, provides a plurality of fingers 42 which extend from a central body 36A in two rows 32A and 34A. The central body 36A is elongated. The fingers 42 extend from the central body 36A to one side of a given first plane which is tangent to the central body. The free ends of the fingers lie in a second plane which is parallel to and spaced from the first plane.

Unlike the toothbrush of the Axelsson patent, there is no attachment plate or base plate in the present invention to interfere with the entry by the fingers 42 into the dental sulcus area 30 between tooth and gum 24 in the region between adjacent teeth 26 and 28. Furthermore, the orientation of the two rows of fingers 32A and 34A with respect to each other is chosen so that the gingival papilla 24 will slide between the two rows of fingers 32A and 34A when the apparatus is inserted between teeth. Thus, the rows 32A and 34A are anatomically shaped to conform to the shape of the gingival papilla 24. In the Axelsson patent, no such predetermined shape is disclosed, nor are the disclosed configurations believed to be suitable for use in the dental sulcus region 30 between the gingival papilla 24 and an adjacent tooth.

FIG. 6D illustrates a further embodiment of the flexible member of the present invention. Here, the flexible member 22D retains the plan view arrowhead-like shape; however, the angle "A" between the wing-like structures 32D and 34D varies as a function of the distance from the handle 20. For example, the angle "A" can be smallest toward the tip portion of the flexible member 22D and largest toward the base of the member 22D. In this manner, it can be ensured that somewhere along the insertion of the flexible member between teeth the fingers 48 of the wing-like structures 32D and 34D will be certain to come into contact with the tooth surfaces within the dental sulcus.

FIG. 6E illustrates a further variation of the assembly method shown in FIG. 6B. Here, fingers 42E are sandwiched between a pair of elongated, angled members 52. The angled members 52 extend the length of the flexible member 22E. As before, the fingers 42E can be anatomically shaped as part of the assembly process by simply choosing the angle of the angled members 52 according to the gingival papilla shape sought to be accommodated. The angled members 52, as well as the angled brackets 50, can be constructed of metal or a stiff plastic, as well as of any other material which can be molded or formed into the desired angled shape. Additionally, these members 52 and 50 can have a "U" shape to provide a "U" shaped cross sectional flexible member 22.

The terms and expressions which have been employed here are used as terms of description, and not of limitation, and there is no intention, in the use of such terms and expressions of excluding equivalents of the features shown and described, or portions thereof, it being recognized that various modifications are possible within the scope of the invention claimed.

What is claimed is:

1. An interproximal dental stimulator and cleaning apparatus of the type which is manipulated by handle means, for use in the dental sulcus region between a tooth and adjacent interproximal gingival papilla, comprising:

a first flexible member, having a broad end, a tip, and a longitudinal axis which extends from the broad end to the tip, the broad end of the member being attached to the handle means, the member including, first and second elongated, wing-like structures which extend along, and project a predetermined outward distance from, the longitudinal axis, the outward distance being largest at the broad end of the member and decreasing in magnitude toward the tip, so that the member has a generally arrowhead-like shape, wherein each wing-like structure comprises a plurality of fingers which provide cleaning and stimulating surfaces, and furtherwherein the member is shaped so that it can be inserted between adjacent teeth so that the interproximal gingival papilla between the teeth is accepted between the first and second wing-like structures, and so that the structures occupy and can be manipulated within the dental sulcus regions between the papilla and teeth.

2. The dental stimulator and cleaning apparatus, as recited in claim 1, wherein the first and second wing-like structures are positioned with respect to each other so that a cross-section of the member taken at right angles to the longitudinal axis has a "V" shape.

3. The dental stimulator and cleaning apparatus, as recited in claim 1, wherein each wing-like stucture curves outward from the longitudinal axis of the member so that a cross-section of the member taken at right angles to the longitudinal axis has a "U" shape.

4. The dental stimulator and cleaning apparatus, as recited in claims 1, 2 or 3, wherein the plurality of fingers comprise flexible bristles positioned in a row.

5. The dental stimulator and cleaning apparatus, as recited in claims 1, 2, or 3, wherein the plurality of fingers are elongated and are constructed from a flexible material.

6. The dental stimulator and cleaning apparatus, as recited in claim 5, wherein the fingers have squared-off tips.

7. The dental stimulator and cleaning apparatus, as recited in claim 5, wherein the fingers have rounded-off tips.

8. The dental stimulator and cleaning apparatus, as recited in claims 1, 2, or 3, wherein each of the plurality of fingers are closely spared to one another and are positioned to extend at right angles to the longitudinal axis of the member.

9. The dental stimulator and cleaning apparatus, as recited in claims 1, 2, or 3, wherein each of the plurality of fingers are teeth-like.

10. The dental stimulator and cleaning apparatus, as recited in claims 1, 2, or 3, wherein the winglike structures project outward in a predetermined general direction and further wherein the member is curved along the longitudinal axis in a direction opposite the direction of outward projection of the wing-like structures.

11. The dental stimulator and cleaning apparatus, as recited in claims 1, 2, or 3, further including a reinforcing rib which is disposed generally along the longitudinal axis of the member.

12. The dental stimulator and cleaning apparatus, as recited in claim 11, wherein the rib is constructed of twisted wire.

13. The dental stimulator and cleaning apparatus, as recited in claim 11, wherein the flexible member is constructed from plastic and further wherein the reinforcing rib is formed by a ridge of plastic positioned generally along the longitudinal axis.

14. The dental stimulator and cleaning apparatus, as recited in claims 1, 2, or 3, wherein the handle means comprises an elongated handle which is angled a predetermined amount at a predetermined distance from the point at which the member is attached to the handle, the member being attached to one end of the handle.

15. The dental stimulator and cleaning apparatus, as recited in claims 1, 2, or 3, wherein the first flexible member is positioned at one end of the handle means and a second flexible member, identical to the first flexible member, is positioned at the opposite end but on the same side of the handle means so that the wing-like structures of the first member project in the same directions as the wing-like structures of the second member.

16. The dental stimulator and cleaning apparatus, as recited in claims 1, 2, or 3, wherein the first flexible member is positioned at one end of the handle means and a second flexible member, identical to the first flexible member, is positioned at the opposite end and opposite side of the handle means so that the wing-like structures of the first member project in the opposite directions as the wing-like structures of the second member.

17. An apparatus for cleansing and stimulating the region between tooth and gingival papilla in the area between adjacent teeth, comprising
a central elongated body having a base and a tip portion;
at least a pair of flexible, wing-like structures projecting away from the central body in different directions and being shaped to accept the gingival papilla between said wing-like structures;
both of said flexible wing-like structures being to one side of a given plane which is tangent to the central body; and
each wing-like structure having a free end lying in a second plane spaced from said central body and including a plurality of elongated flexible fingers.

18. The apparatus of claim 17 wherein the plurality of flexible fingers are disposed along the length of said central body.

19. The apparatus of claim 17 wherein the wing-like structures taper in length along the length of said central body.

20. The apparatus of claim 17 wherein each wing-like structure includes an irregular surface.

21. The apparatus of claim 17 wherein each of the plurality of fingers are closely spaced to form a pattern of parallel ridges projecting from said central body to said free end.

22. The apparatus of claim 20 wherein the irregular surface comprise raised dots.

23. The apparatus of claim 17 wherein the central body includes a plurality of intertwined wires.

24. The apparatus of claim 17 wherein the central body and wing-like structures are formed as an integral structure.

25. The apparatus of claim 17 wherein each of the plurality of fingers are a plurality of teeth-like.

26. The apparatus of claim 25 wherein each of the teeth-like fingers have blunted ends.

27. The apparatus of claim 18 wherein each flexible finger member has a cross section which tapers in magnitude from a maximum adjacent to the central body to a minimum at the free end.

28. The apparatus of claim 17 including a handle which is attached to the base of the central body.

29. The apparatus of claim 28 wherein the handle comprises an elongated member suitable for grasping by the human hand.

30. The apparatus of claim 29 wherein the elongated member is angled a predetermined amount and at a predetermined distance from the central body.

31. The apparatus of claim 1 wherein the first and second wing-like structures are positioned with respect to each other so that a cross section of the member, taken at right angles to the longitudinal axis, is anatomically shaped to conform to the gingival papilla.

32. The apparatus of claim 17 wherein the pair of wing-like structures are disposed with respect to each other to provide a cross section, taken at right angles to the central body, which is anatomically shaped to conform to the gingival papilla.

33. The apparatus of claim 1 wherein the flexible member is sandwiched between a pair of angled brackets, each bracket having a predetermined angle, the brackets being attached at one end to the handle means and having a free end which extends outward along the flexible member.

* * * * *